(12) United States Patent
Razzak et al.

(10) Patent No.: US 8,313,752 B2
(45) Date of Patent: Nov. 20, 2012

(54) MACROCYCLIC LACTONE COMBINATION COMPOSITIONS, VACCINES AND METHODS FOR PRODUCING SAME

(75) Inventors: Majid Razzak, Glenfield (NZ); Robert Holmes, Auckland (NZ)

(73) Assignee: Merial Limited, Duluth, GA (US)

( * ) Notice: Subject to any disclaimer, the term of this patent is extended or adjusted under 35 U.S.C. 154(b) by 253 days.

(21) Appl. No.: 12/759,176

(22) Filed: Apr. 13, 2010

(65) Prior Publication Data

US 2010/0266628 A1  Oct. 21, 2010

(30) Foreign Application Priority Data

Apr. 14, 2009  (NZ) ........................................ 576201
Apr. 20, 2009  (NZ) ........................................ 576391

(51) Int. Cl.
*A61K 39/15* (2006.01)
*A61K 39/215* (2006.01)

(52) U.S. Cl. .................. 424/215.1; 424/221.1
(58) Field of Classification Search .................. None
See application file for complete search history.

(56) References Cited

U.S. PATENT DOCUMENTS

| | | | |
|---|---|---|---|
| 6,214,367 B1 | 4/2001 | Harvey | |
| 6,663,879 B2 * | 12/2003 | Harvey | 424/422 |
| 6,746,677 B2 * | 6/2004 | Cobb et al. | 424/278.1 |
| 6,974,577 B2 * | 12/2005 | Knape et al. | 424/201.1 |
| 6,991,801 B2 | 1/2006 | Soll et al. | |
| 2005/0118222 A1 | 6/2005 | Wolff | |

FOREIGN PATENT DOCUMENTS

| | | |
|---|---|---|
| GB | 2030043 A | 4/1980 |
| GB | 2267707 A | 12/1993 |

OTHER PUBLICATIONS

Walsh et al (Australian Veterinary Journal 72:201-207, 1995).*
Rickard et al (Veterinary Parasitology 41:45-55, 1992).*
Baoliang et al (Veterinary Research Communications 30:263-270, 2006).*

* cited by examiner

*Primary Examiner* — Mary E Mosher
(74) *Attorney, Agent, or Firm* — Judy Jarecki-Black; Chad Kitchen; Merial Limited

(57) ABSTRACT

An injectable composition, capable of preventing or controlling parasitic, viral, or bacterial infections or diseases, for example scours, in pregnant cows and viral infections or diseases in neonatal calves by parenterally administering to each cow in a herd of pregnant cows, a dose of a combination composition comprising: (a) at least one inactivated viral component derived from rotavirus and/or coronavirus; (b) a macrocyclic lactone active compound; and (c) a pharmaceutically acceptable parenteral carrier and preservative. The injectable compositions which include eprinomectin result in extremely low milk residues.

18 Claims, 5 Drawing Sheets

MACROCYCLIC LACTONE COMBINATION COMPOSITIONS, VACCINES AND METHODS FOR PRODUCING SAME

CROSS REFERENCE TO RELATED APPLICATIONS

This application claims benefit of the NZ provisional application Serial No. 576201 filed on Apr. 14, 2009, and of NZ provisional application Serial No. 576391 filed on Apr. 20, 2009.

FIELD OF THE INVENTION

This invention relates to improvements in the field of veterinary remedies and more particularly to improvements in relation to combination vaccine formulations providing protection against parasites as well as the viruses and/or bacteria that are the causative factors in neonatal scouring of calves.

BACKGROUND OF THE INVENTION

The successful calving of the cow and its transition to lactation are two critical keys to cattle farm productivity. For the farmer to achieve their productivity goal there are two critical disease challenges that must be overcome:

Parasitism in the cow—The energy demand of the unborn calf can place the pregnant cow under great stress. As a result body condition suffers and the immune system becomes less effective at warding off infection. One of the major types of infection is parasitism. Usually adult cattle have a high degree of immunity to parasite infection but this is not the case during the calving period.

To help the cow overcome any acquired parasite burden farmers may treat cows during pregnancy with anthelmintics. These products are drugs designed to kill resident worm populations, and in some cases, prevent further infection for a period of time. Historically drugs such as levamisole, oxfendazole, fenbendazole, albendazole, abamectin and ivermectin have been used. These are administered in oral, injectable or topical form. However they have the disadvantage that there is a risk of residues of these anthelmintic drug being present in the milk of the cow after calving has occurred and lactation has commenced. In some countries, such anthelmintics cannot be used to treat animals whose milk is to be used for human consumption, while in other countries, the treatment period before lactating commences must be in excess of 60 days.

Scours in the Calf—The most common cause of calf morbidity in the neonatal period is diarrhea. The major cause of this diarrhea is the presence of scour-causing bacteria and viruses, including *Escherichia coli, Clostridium perfringens*, Rotavirus and Coronavirus; often in combination and/or with other bacteria, viruses and intestinal parasites.

Viruses—Rotavirus infection is the most common viral cause of diarrhea in calves. Groups A and B rotavirus are involved, but group A is most prevalent and clinically important and contains several serotypes of differing virulence. Rotavirus replicates in the mature absorptive and enzyme-producing enterocytes on the villi of the small intestine, leading to rupture and sloughing of the enterocytes with release of virus to infect adjacent cells. Rotavirus does not infect the immature cells of the crypts. With virulent strains of rotavirus, the loss of enterocytes exceeds the ability of the intestinal crypts to replace them; hence, villous height is reduced, with a consequent decrease in intestinal absorptive surface area and intestinal digestive enzyme activity.

Coronavirus is also commonly associated with diarrhea in calves. It replicates in the epithelium of the upper respiratory tract and in the enterocytes of the intestine, where it produces similar lesions to rotavirus but also infects the epithelial cells of the large intestine to produce atrophy of the colonic ridges.

Bacteria—*E. coli* infection is the most important bacterial cause of diarrhea in calves; at least 2 distinct types of diarrheal disease are produced by different strains of this organism. One type is associated with enterotoxigenic *E. coli*, which has 2 virulence factors associated with the production of diarrhea. Fimbrial antigens enable the bacteria to attach to and colonize the villi of the small intestine. Strains present in calves most commonly possess K99 (F5) or F41 fimbrial antigens, or both. These antigens are the focus of immunologic protection. Enterotoxigenic *E. coli* also express a thermostable, nonantigenic enterotoxin (Sta) that influences intestinal ion and fluid secretion to produce a noninflammatory secretory diarrhea. Diarrhea in calves and lambs also has been associated with enteropathogenic *E. coli* that adhere to the intestine to produce an attaching and effacing lesion, with dissolution of the brush border and loss of microvillus structure at the site of attachment, a decrease in enzyme activity, and changes in ion transport in the intestine. These entero-pathogens are also called "attaching and effacing *E. coli*." Some produce verotoxin, which may be associated with a more severe hemorrhagic diarrhea. The infection most frequently is in the cecum and colon, but the distal small intestine can also be affected. The damage in severe infections can result in edema and mucosal erosions and ulceration, leading to hemorrhage into the intestinal lumen.

*Clostridium perfringens* types A, B, C, and E produce a variety of necrotizing toxins which cause a rapidly fatal hemorrhagic enteritis in calves. The disease in calves is rare and usually sporadic.

At present, anthelmintic treatment of pregnant cows is achieved with a dedicated anthelmintic formulation (oral, topical and/or injectable). These formulations currently do not contain any form of vaccine treatment able to provide protection to the new born calf. However, a number of scours-only vaccines are currently marketed for use in cattle. These vaccines are generally classified as inactivated, referring to the fact that the vaccine contains killed virus or bacterial components. Typically these vaccines will contain inactivated strains providing protection from a number of the causative elements of scouring (rotavirus, coronavirus, *E. coli*, clostridial diseases) Cows are treated with the vaccine usually by deep intramuscular injection with a dose of between 2-5 mL. This treatment as an annual booster soon before calving provides a strong increase in antibodies in the colostrum available to the calf immediately after calving. Calves fed colostrum from vaccinated cows during the first two to four weeks of life have been demonstrated to have:

Reduced incidence of scours caused by rotavirus and coronavirus

Reduced shedding of virus due to infection with rotavirus or coronavirus

Reduced severity of diarrhea caused by *E. coli*.

Typical scour vaccines of this kind available in the United States include:

GUARDIAN® (Schering-Plough). This is a multi-component vaccine which includes *Escherichia coli* K99 antigen, two inactivated coronaviruses, two G-types of inactivated rotaviruses, and bacterin-toxoid from *Clostridium perfringens* Types C and D. GUARDIAN is recommended for use in pregnant cattle as an aid in the prevention of neonatal calf diarrhea caused by enterotoxigenic *E. coli* pilus type K99, bovine Group A Serotype G6 rotaviruses, enterotoxemia caused by *C. perfringens* Types C and D, and as an aid in the control of neonatal calf diarrhea caused by bovine coronaviruses.

SCOURBOS 9 (Novartis). Another multi-component vaccine which includes, four different *E. coli* strains, three inactivated rotaviruses (serotypes G10, G6 and G8), inactivated Coronavirus and *Clostridium perfringens* Type C bacterin-toxoid. SCOURGUARD (Pfizer). A combination of inactivated bovine rotavirus (serotypes G10, G6), inactivated coronavirus, and *E. coli* K99 bacterin-toxoid.

For all three vaccines, a 2 mL dose is administered via deep intramuscular injection. There is no milk withholding period applied to any of the treatments. Treatment programs rely on a two dose treatment schedule in the first year of use, then a single annual booster dose given each year prior to calving. The recommended time at which the treatments should be given (in weeks prior to calving) is outlined in Table 1.

TABLE 1

| | First Year of Treatment (treatment time in weeks prior to calving) | | Annual booster (treatment time in weeks prior to calving) |
|---|---|---|---|
| | Initial Dose | Booster Dose | |
| GUARDIAN | 12 weeks | 9-6 weeks | 7-5 weeks |
| SCOURBOS | 16-8 weeks | 4 weeks | 10-8 weeks |
| SCOURGUARD | 9-6 weeks | 6-3 weeks | 6-3 weeks |

The difference in treatment times is explained by the claimed relative effectiveness of the vaccine antigens used with each vaccine. However it should be noted that the closest number of weeks to calving in which the three treatments are recommended to be administered is 5 weeks (GUARDIAN annual booster), 4 weeks (SCOURBOS Booster Dose) and 3 weeks (SCOURGUARD Booster Dose and Annual Booster). In the best case this is only 35 days from calving while in the worst case it is 21 days from calving.

Attaining high levels of antibody in the colostrum through the use of potent vaccines has proven extremely effective in preventing calf scours. The most effective vaccination program is one in which the level of antibodies in the cows system peaks at or just prior to calving, providing maximum protection to the calf via the colostrum. For this purpose there is a requirement that the annual booster vaccine be given reasonably close to calving.

There is another reason why vaccine manufacturers need to design their products with the possibility that vaccination will occur close to calving. This reason is that typically vaccination will occur on a whole herd basis. Cows within a herd will be due to calve on different dates over a period of several weeks or months. The width of the calving span and the unpredictability of actual calving date can make it very difficult to select the ideal time to treat. For best effect, vaccines might be administered 21-35 days (according to the vaccine) prior to the earliest expected calving date within the herd or 21-35 days prior to the mean expected calving date within the herd. Some cows may calve soon after vaccination while others may calve many weeks later. Furthermore, the unpredictability of actual calving date compared to expected calving date can mean that some cows will calve much less than 21-35 days after treatment and potentially as early as the day of treatment. This short treatment to calving interval eliminates the possibility of using many anthelmintic active compounds designed to treat pregnant cows from any potential scours vaccine combination.

Vaccines containing both macrocyclic lactones and antigens, including for example peptides, membrane fractions, inactivated pathogens, and the like, are challenging to formulate due to solvent/dispersant incompatibilities. There are previous reports of combining active ingredients plus vaccines, but very few of them describe combining macrocyclic lactones plus a vaccine. One possible reason for this is that it is well known in the art that macrocyclic lactones are susceptible to degradation in the presence of other actives or in certain solvent systems, particularly aqueous solvent systems. For example, GB-A-2030043 describes injectable combinations of a non-macrocyclic lactone active (tetramisole) plus a vaccine. Importantly, the application does not disclose compositions comprising dispersing agents, which is an important component in injectable aqueous macrocyclic lactone compositions. Umehara et al report that combining one macrocyclic lactone, doramectin, with a foot-and-mouth disease vaccine may result in interference (Rev. Brasil. Parasitol. Vet., 1993, 2(2): 141-144). Other examples include JP-A-62294623, which discloses oral compositions comprising antibiotics and deactivated *Salmonella*, and GB-A-2267707, which describes macrocyclic lactones in optional combination with vaccination. U.S. Pat. No. 6,746,677B2 to Cobb (Wyeth, Fort-Dodge Animal Health) generally describes compositions comprising macrolide compounds or mixtures thereof, a water soluble organic solvent, a dispersing agent, an adjuvant, at least one antigen, and saline or water or a mixture thereof. In addition, patent application US 2005/0118222 A1 to Wolff describes simultaneously carrying, by means of an injection, macrocyclic lactone and an antigen against ticks. In another example, U.S. Pat. No. 6,663,879 and US U.S. Pat. No. 6,214,367 to Harvey describe stable injectable compositions that include a non-aqueous parasitic agent in a therapeutically effective amount, chosen from the group of avermectin, ivermectin, doramectin, abamectin, milbemycin and moxidectin, and an antigen in combination with a liquid carrier that also acts as an adjuvant.

The instant invention solves the problem of combining macrocyclic lactones with vaccines by using a novel and nonobvious solvent system. Unlike the alcohol solvents taught Cobb, Applicants have found that dimethyl acetamide (DMA) combined with specific surfactants provides exceptionally stable and high concentration combined macrocyclic lactone/vaccine formulations. The resulting effective dose volume is desirably lower than previous compositions.

Accordingly, there is a real and unsatisfied need in the art for a convenient means to treat pregnant cows that: protects the cow from the effects of parasitism while avoiding anthelmintic residues in milk; reduces the risk of scours in the new born calf due to viral and bacterial diseases; and provides the farmer with the ability to treat cows reasonably close to calving.

SUMMARY OF THE INVENTION

Therefore the problem addressed by this invention is the need to provide a convenient anthelmintic/vaccine treatment for farmers that maintains the health of cow/calf combinations while ensuring there is no contamination of milk with drug residues, or which will at least provide the farmer with a useful choice.

In one aspect the invention provides a method of preventing or controlling parasitic diseases in pregnant cows and viral diseases in neonatal calves by parenterally administering to the pregnant cow an effective amount of a combination composition containing at least one viral component, such as inactivated rotavirus or inactivated coronavirus, together with one or more macrocyclic lactone active compound, for example, eprinomectin, and a suitable parenteral carrier and preservative. The macrocyclic lactone active or actives may include, but in no way be limited to, abamectin, dimadectin, doramectin, emamectin, eprinomectin, ivermectin, latidectin, lepimectin, selamectin, milbemectin, milbemycin D, milbemycin oxime, moxidectin or nemadectin Another aspect of the instant invention provides for the combination compositions used in said methods.

In another aspect the method may also control infection by disease-causing bacteria such as E. coli by including with the inactivated viral component an E. coli bacterin-toxoid and/or a bacterin-toxoid produced by other disease-causing bacteria.

The same dose volume may be administered to cattle weighing from 400 kg to 800 kg. This has the advantage that a herd of pregnant cows can be quickly treated by applying the same dose volume regardless of the weight of each cow as a typical herd consists of cows within that weight range. Alternatively, the weight brackets for each dose may be restricted so that the invention may deliver a macrocyclic lactone active dose of 200 µg/kg to 400 µg/kg.

In another aspect the invention provides an injectable composition for preventing or controlling both parasitic diseases and viral diseases in cattle, the composition containing (a) an effective amount of at least one viral component selected from the group consisting of inactivated rotavirus, and inactivated coronavirus, (b) a macrocyclic lactone anthelmintic active compound such as abamectin, doramectin, eprinomectin, ivermectin, moxidectin (c) a suitable carrier, and (d) a preservative. The injectable composition may include an E. coli bacterin-toxoid.

In another aspect the invention provides a method of preventing or controlling parasitic diseases in pregnant cows and scours in neonatal calves by parenterally administering to the pregnant cow an effective amount of a combination composition containing a macrocyclic lactone active compound and a viral component selected from the group comprising inactivated rotavirus, inactivated coronavirus and E. coli bacterin-toxoid. In some aspects, the macrocyclic lactone is eprinomectin.

Unless otherwise defined in specific examples, the term "effective amount", as used herein, generally means an amount of active or vaccine component that is sufficient to cause a "biologically useful effect" in an animal. The "biologically useful effect" may include, for example: prevention or control of parasites in or on animals, stimulation of an immune response that protects said animals from subsequent challenge with disease or disorder-causing agents or pathogens, or any other effect that a skilled person will readily appreciate as being beneficial, protective and/or conducive to the maintenance or improvement of the animal's health, well-being, productivity, longevity, resistance to disease, and the like.

These and other embodiments are described in, or are obvious from and encompassed by, the following Detailed Description.

BRIEF DESCRIPTION OF THE DRAWINGS

The following detailed description, given by way of examples, but not intended to limit the invention solely to the specific embodiments described, may best be understood in conjunction with the accompanying drawings, in which.

DETAILED DESCRIPTION

Figure 1:
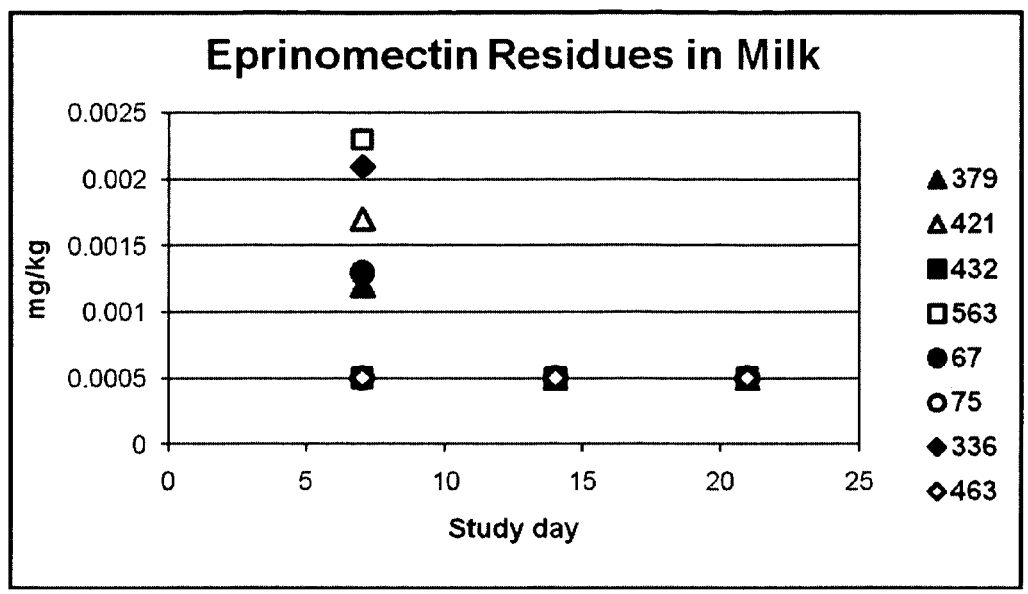
FIG. 1 is a graph of eprinomectin residues in milk

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

It is to be understood that both the foregoing general description and the following detailed description are exemplary and explanatory only and are not restrictive of the invention as claimed.

The present invention provides combination compositions that are effective for preventing or controlling parasitic, bacterial, or viral infections in cattle comprising (a) an effective amount of a viral component, which comprises at least one inactivated rotavirus or coronavirus, and (b) at least one macrocyclic lactone active agent in a pharmaceutically acceptable carrier.

The viral component can be a commercially available vaccine, for example, Merial's RESPISHIELD™ or RELI- ANT® bovine vaccines. The RELIANT® 4 vaccines, for example, include eight antigen combinations, allowing significant flexibility to combination compositions of the instant invention. The viral component may comprise any number of well-known adjuvants, for example, Merial's TS6 adjuvant described for example in U.S. Pat. No. 7,371,395 to Parisot et al. The TS6 adjuvant is currently successfully used, for example, in Merial's SWIVAX™-MH Needle-Free *M. hyopneumoniae* vaccine for swine. The adjuvant may also be Merial's LR4 adjuvant, described for example in U.S. Pat. No. 7,691,368 also to Parisot et al. The invention is therefore intended to encompass combination compositions which may be usefully applied to at least bovine and porcine animals.

Also provided are methods for the prevention or control of parasitic, bacterial, or viral infections, which comprise administering an effective amount of the compositions of the invention to the animal in need thereof.

The macrocyclic lactone anthelmintic compounds contemplated in this invention are well known to an ordinarily skilled practitioner. These compounds include avermectins and milbemycins, collectively known as the macrocyclic lactone class of anthelmintic active compounds. For avermectins, ivermectin and abamectin, reference may be made, for example, to the publication "Ivermectin and Abamectin", 1989, by M. H. Fischer and H. Mrozik, William C. Campbell, published by Springer Verlag., "Macrocyclic Lactones in Antiparasitic Therapy", 2002, by J Vercruysse and R S Rew published by CABI Publishing or Albers-Schönberg et al. (1981), "Avermectins Structure Determination", *J. Am. Chem. Soc.*, 103, 4216-4221. For doramectin, "Veterinary Parasitology", vol. 49, No. 1, Jul. 1993, 5-15 may be consulted. For milbemycins, reference may be made, inter alia, to Davies H. G. et al., 1986, "Avermectins and Milbemycins", *Nat. Prod. Rep.*, 3, 87-121, Mrozik H. et al., 1983, Synthesis of Milbemycins from Avermectins, *Tetrahedron Lett.*, 24, 5333-5336, U.S. Pat. No. 4,134,973 and EP 0 677 054, all of which are incorporated herein by reference.

Macrocyclic lactones are either natural products or are semi-synthetic derivatives thereof. The structures of the avermectins and milbemycins are closely related, e.g., by sharing a complex 16-membered macrocyclic lactone ring; milbemycins lack the glycosidic moiety of the avermectins. The natural products avermectins are disclosed in U.S. Pat. No. 4,310,519 to Albers-Schönberg et al., and the 22,23-dihydro avermectin compounds are disclosed in Chabala et al., U.S. Pat. No. 4,199,569. Mention is also made of Kitano, U.S. Pat. No. 4,468,390, Beuvry et al., U.S. Pat. No. 5,824,653, EP 0 007 812 A1, U.K. Patent Specification 1 390 336, EP 0 002 916, and Ancare New Zealand Patent No. 237 086, inter alia. Naturally occurring milbemycins are described in Aoki et al., U.S. Pat. No. 3,950,360 as well as in the various references cited in "The Merck Index" 12th ed., S. Budavari, Ed., Merck & Co., Inc. Whitehouse Station, N.J. (1996). Latidectin is described in the "International Nonproprietary Names for Pharmaceutical Substances (INN)", *WHO Drug Information*, vol. 17, no. 4, pp. 263-286, (2003). Semisynthetic derivatives of these classes of compounds are well known in the art and are described, for example, in U.S. Pat. No. 5,077,308, U.S. Pat. No. 4,859,657, U.S. Pat. No. 4,963,582, U.S. Pat. No. 4,855,317, U.S. Pat. No. 4,871,719, U.S. Pat. No. 4,874,749, U.S. Pat. No. 4,427,663, U.S. Pat. No. 4,310,519, U.S. Pat. No. 4,199,569, U.S. Pat. No. 5,055,596, U.S. Pat. No. 4,973,711, U.S. Pat. No. 4,978,677, U.S. Pat. No. 4,920,148 and EP 0 667 054, all incorporated herein by reference.

Non-limiting examples of compounds belonging to this class are represented by Formula (I):

Formula (I)

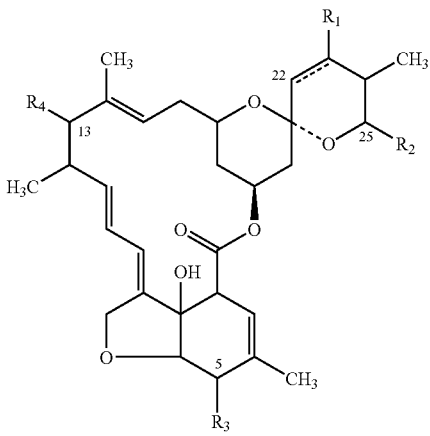

where the broken line indicates a single or a double bond at the 22,23-positions;
$R_1$ is hydrogen or hydroxy provided that $R_1$ is present only when the broken line indicates a single bond;
$R_2$ is alkyl of from 1 to 6 carbon atoms or alkenyl of from 3 to 6 carbon atoms or cycloalkyl of from 3 to 8 carbon atoms; $R_3$ is hydroxy, methoxy or $=NOR_5$ where $R_5$ is hydrogen or lower alkyl; and $R_4$ is hydrogen, hydroxy or

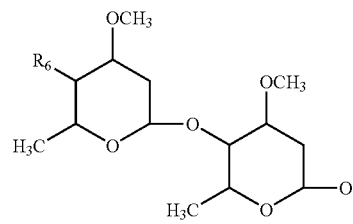

where $R_6$ is hydroxy, amino, mono- or di-lower alkylamino or lower alkanoylamino.

In some embodiments, the compounds are avermectin B1a/B1b (abamectin), 22,23-dihydro avermectin B1a/B1b (ivermectin) and the 4"-acetylamino-5-ketoximino derivative of avermectin B1a/B1b. Both abamectin and ivermectin are approved as broad spectrum antiparasitic agents. Abamectin and ivermectin structures are represented by Formula (II):

Formula (II)

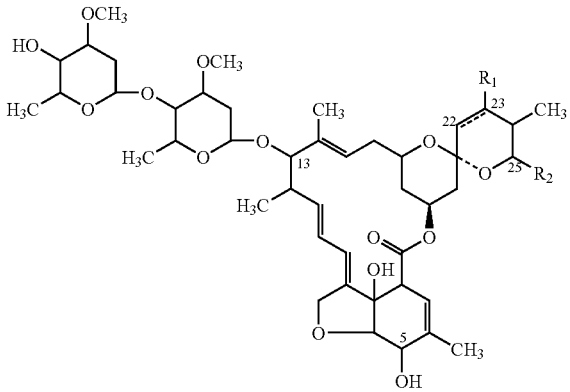

wherein $R_1$ and $R_2$ are as defined above for formula (I). For abamectin the broken line represents a double bond and $R_1$ is not present and for ivermectin the double bond represents a single bond and $R_1$ is hydrogen; and $R_2$ is isopropyl or sec-butyl.

The 4"-acetyl amino-5-ketoximino derivatives of avermectin B1a/B1b are represented by Formula (III):

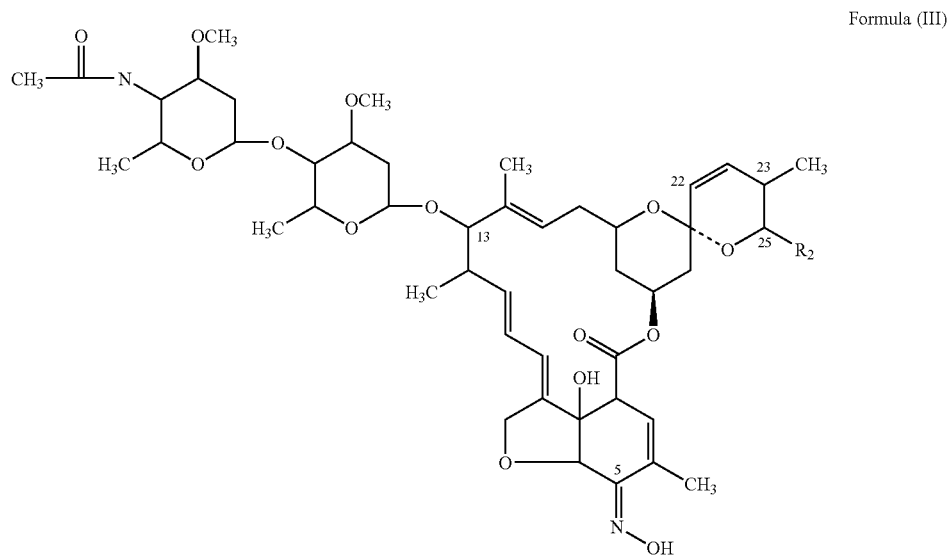

Formula (III)

where $R_2$ is isopropyl or sec-butyl.

In some embodiments, the avermectin products may be prepared as a mixture comprising at least 80% of a compound according to Formula (II or III) wherein $R_2$ is sec-butyl and no more than 20% of a compound according to Formula (II or III) wherein $R_2$ is isopropyl.

In other embodiments, the avermectins may include emamectin, eprinomectin and doramectin. Doramectin has a structure according to Formula (IV):

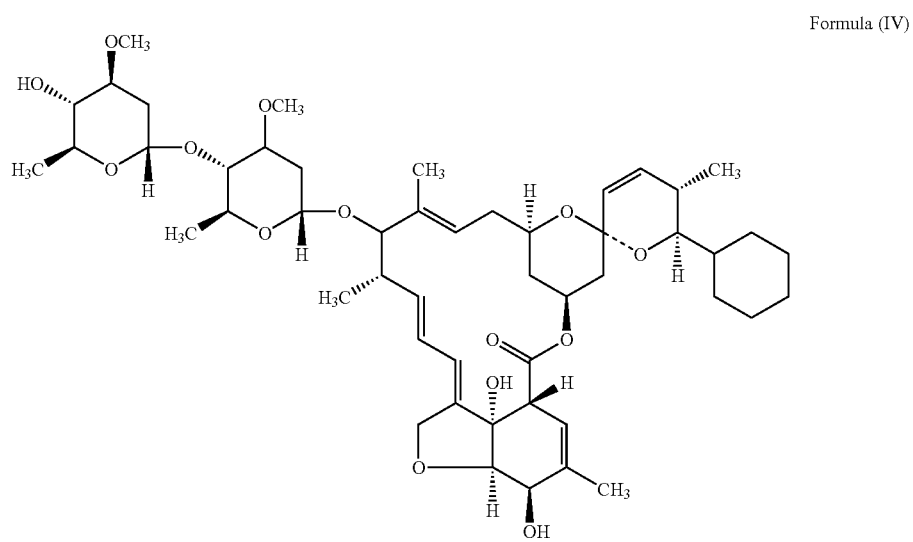

Formula (IV)

Eprinomectin is disclosed in U.S. Pat. No. 4,427,663 (incorporated herein by reference), and has a structure according to Formula (V):

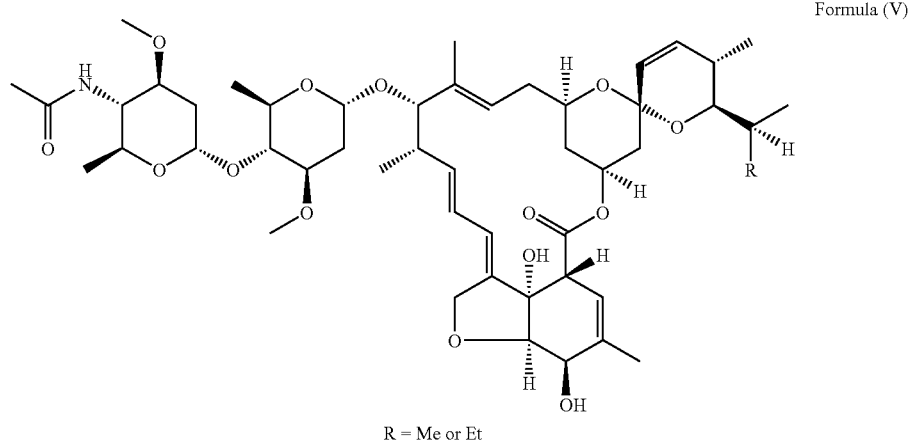

Formula (V)

R = Me or Et

In some embodiments of the instant invention, the milbemycin is moxidectin, represented by Formula (VI);

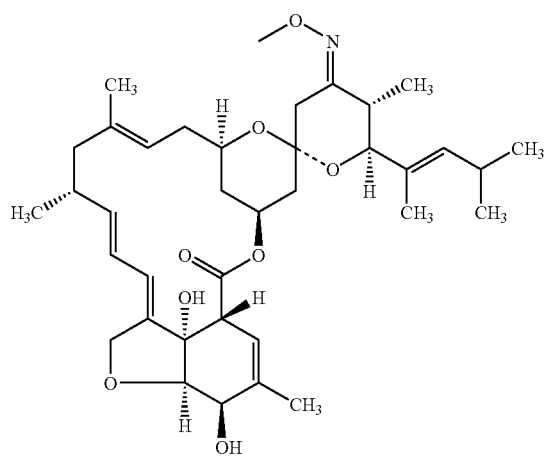

Formula (VI)

Some embodiments may include the monosaccharide avermectin derivatives which have an oxime substitution on the 5-position of the lactone ring. Other embodiments include milbemycins such as milbemycin $\alpha_1$, which is represented by Formula (VII).

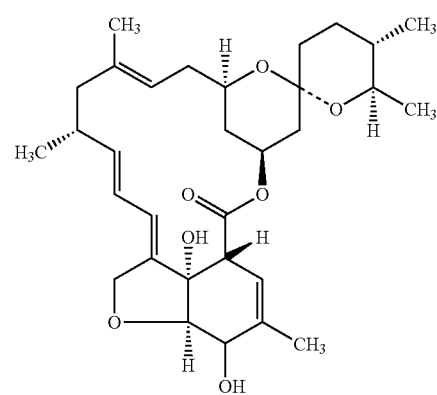

Formula (VII)

Also contemplated within the scope of the invention are acid or base salts of the compounds in the compositions of the invention, where applicable.

The term "acid" contemplates all pharmaceutically acceptable inorganic or organic acids. Inorganic acids include mineral acids such as hydrohalic acids such as hydrobromic acid and hydrochloric acid, sulfuric acid, phosphoric acids and nitric acid. Organic acids include all pharmaceutically acceptable aliphatic, alicyclic and aromatic carboxylic acids, dicarboxylic acids, tricarboxylic acids and fatty acids. In one embodiment of the acids, the acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, acetic acid, propionic acid, isopropionic acid, valeric acid, α-hydroxy acids such as glycolic acid and lactic acid, chloroacetic acid, benzoic acid, methane sulfonic acid, and salicylic acid. Examples of dicarboxylic acids include oxalic acid, malic acid, succinic acid, tartaric acid, fumaric acid, and maleic acid. An example of a tricarboxylic acid is citric acid. Fatty acids include all pharmaceutically acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically acceptable inorganic or organic bases, including hydroxides, carbonates or bicarbonates of alkali metal or alkaline earth metals. Salts formed with such bases include, for example, the alkali metal and alkaline earth metal salts, including, but not limited to, as the lithium, sodium, potassium, magnesium or calcium salts. Salts formed with organic bases include the common hydrocarbon and heterocyclic amine salts, which include, for example, ammonium salts ($NH4^+$), alkyl- and dialkylammonium salts, and salts of cyclic amines such as the morpholine and piperidine salts.

In addition, the compounds within the compositions of the invention may exist as hydrates or solvates, in which a certain stoichiometric amount of water or a solvent is associated with the molecule in the crystalline form. The compositions of the invention may include hydrates and solvates of the active agents.

Terms used herein will have their customary meaning in the art unless specified otherwise. The term "alkyl" refers to saturated straight, branched, cyclic, primary, secondary or tertiary hydrocarbons, including those having 1 to 12 atoms. In some embodiments, alkyl groups will include $C_1$-$C_{10}$, $C_1$-$C_8$, $C_1$-$C_6$ or $C_1$-$C_4$ alkyl groups. Examples of $C_1$-$C_{10}$ alkyl include, but are not limited to, methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "lower alkyl" refers to alkyl groups as defined above, which have 1-3 carbon atoms.

In some embodiments, the present invention may include compositions which are effective in treating and/or preventing endoparasite infestations. Said endoparasites may include helminths such as *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus.*

Helminths also include *Anaplocephala, Ancylostoma, Anecator, Ascaris, Capillaria, Cooperia, Dipylidium, Dirofilaria, Echinococcus, Enterobius, Fasciola, Haemonchus, Oesophagostumum, Ostertagia, Toxocara, Strongyloides, Toxascaris, Trichinella, Trichuris,* and *Trichostrongylus.* Or others from the class of helminths, such as from the class of helminths, for example, *Ancylostoma duodenale, Ancylostoma ceylanicum, Acylostoma braziliensis, Ancylostoma* spp., *Ascaris lubricoides, Ascaris* spp., *Brugia malayi, Brugia timori, Bunostomum* spp., *Chabertia* spp., *Clonorchis* spp., *Cooperia* spp., *Dicrocoelium* spp, *Dictyocaulus filaria, Diphyllobothrium latum, Dracunculus medinensis, Echinococcus granulosus, Echinococcus multilocularis, Enterobius vermicularis, Faciola* spp., *Haemonchus* spp., *Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britovi, Trichinella nelsoni, Trichinella pseudopsiralis, Trichostrongulus* spp., *Trichuris trichuria,* and *Wuchereria bancrofti.*

When administered topically to cattle, Eprinomectin is not metabolized extensively and the parent compound makes up 90% of residues in tissues and more than 85% in feces. Eprinomectin also has a relatively low milk-plasma coefficient ($\leq 0.2$) indicating greater partitioning of compound away from milk and into plasma. In contrast, many other macrocyclic lactone compounds may have milk-plasma coefficients of around 1.0. Active compounds that have a milk-plasma coefficient equal to 1.0 are defined herein (and will be understood by an ordinarily skilled person) to have no tendency to partition either toward or away from milk. Alvinerie et al. (1999) examined the pharmacokinetics of eprinomectin in lactating cattle and concluded that only 0.1% of the total dose was eliminated in the milk, which was 50-fold less than that observed for either ivermectin or moxidectin.

When administered topically eprinomectin or other macrocyclic lactone active compounds may be administered at a dose of about 500 µg/kg bodyweight. When administered via subcutaneous injection, macrocyclic lactone treatments are typically administered at a dose of about 100 µg/kg to about 400 µg/kg. These doses appear to be sufficient to achieve efficacy against a broad range of parasites with varying levels of susceptibility to the various macrocyclic lactone active compounds.

In some embodiments, formulations or compositions according to the present invention may contain from approximately 0.5% w/v to approximately 10% w/v of eprinomectin or another macrocyclic lactone active compound; the dose may be delivered to the animal from about 100 µg/kg to about 400 µg/kg, or from about 200 µg/kg to about 300 µg/kg.

In another embodiment, a standard dose and volume of formulations according to the present invention will be effective in preventing and/or treating or illness, disease, disorders or infestations in animals weighing from 400 kg to 800 kg.

In other embodiments, animals weighing 600 kg and above will receive a standard dose and volume while animals weighing from 599 kg to 400 kg to receive a dose approximately 75% of the size of said standard dose. Table 2 provides sample dose sizes when compositions according to the instant invention comprise Eprinomectin.

In an embodiment, compositions according to the instant invention comprise a macrocyclic lactone, for example, eprinomectin, an eprinomectin solvent system, at least one viral component, and suitable surfactants to enable the macrocyclic lactone and the viral component to form a stable, pharmaceutically acceptable composition.

In one embodiment, the composition comprises eprinomectin, the solvent system comprises DMA (dimethyl acetamide) and MYGLYOL (propylene glycol diesters of caprylic and capric acids), and the viral component is derived from rotavirus or coronavirus.

In another embodiment, the composition additionally comprises surfactants such as SPAN or TWEEN, which surfactants function to facilitate the formation of a stable multiple emulsion between completely dissolved eprinomectin, surfactants, and the at least one viral component. In some embodiments, effective dose amounts are indicated by Table 2.

TABLE 2

Eprinomectin composition delivered doses by animal weight.

| Dose size/eprinomectin concentration in formulation | Animal Weight | Dose delivered |
|---|---|---|
| 5 mL/3.2% w/v | 400 kg | 400 μg/kg |
| 5 mL/3.2% w/v | 500 kg | 320 μg/kg |
| 5 mL/3.2% w/v | 600 kg | 266 μg/kg |
| 5 mL/3.2% w/v | 700 kg | 228 μg/kg |
| 5 mL/3.2% w/v | 800 kg | 200 μg/kg |

Table 3 provides sample dose sizes when compositions according to the instant invention comprise Ivermectin.

TABLE 3

Ivermectin composition delivered doses by animal weight.

| Dose size/ivermectin concentration in formulation | Animal Weight | Dose delivered |
|---|---|---|
| 3 mL/4.0% w/v | 400 kg | 300 μg/kg |
| 3 mL/4.0% w/v | 500 kg | 240 μg/kg |
| 3 mL/4.0% w/v | 599 kg | 200 μg/kg |
| 4 mL/4.0% w/v | 600 kg | 266 μg/kg |
| 4 mL/4.0% w/v | 700 kg | 228 μg/kg |
| 4 mL/4.0% w/v | 800 kg | 200 μg/kg |

In another embodiment, compositions according to the instant invention may be prepared using the steps comprising: (a) preparing a macrocyclic lactone solution component; (b) preparing a vaccine component which is suitable for treating neonates; and (c) blending components (a) and (b) to produce the compositions. In yet another embodiment, the compositions are stable emulsions and suitable for injection into an animal, for example a bovine, porcine, caprine, ovine, or equine animal.

In some embodiments where eprinomectin is used, the macrocyclic lactone solution component may comprise DMA (dimethyl acetamide) and MIGLYOL (propylene glycol diesters of caprylic and capric acids), the surfactants may include Lecithin and SPAN, and the viral component may be derived from rotaviruses or coronaviruses. Compositions may optionally further comprise components from disease-causing bacteria or protists, for example, *E. coli* bacterin-toxoid.

Compositions according to the instant invention may comprise components according to Tables 4-8.

TABLE 4

| | (% w/v) |
|---|---|
| Eprinomectin (Ivermectin) | 8% (4%) |
| Dimethyl acetamide | 15% |
| MIGLYOL 840 | 55% |
| Surfactants | 5% |
| Vaccine/adjuvant/water blend | to vol. |

TABLE 5

| | (% w/v) |
|---|---|
| Abamectin | 4% |
| Dimethyl acetamide | 15% |
| MIGLYOL 840 | 55% |
| Surfactants | 5% |
| Vaccine/adjuvant/water blend | to vol. |

TABLE 6

| | (% w/v) |
|---|---|
| moxidectin | 4% |
| Dimethyl acetamide | 15% |
| MIGLYOL 840 | 55% |
| Surfactants | 5% |
| Vaccine/adjuvant/water blend | to vol. |

TABLE 7

| | (% w/v) |
|---|---|
| Eprinomectin | 4% |
| Dimethyl acetamide | 15% |
| MIGLYOL 840 | 55% |
| Surfactants | 5% |
| Vaccine/adjuvant/water blend | to vol. |

TABLE 8

| | (% w/v) |
|---|---|
| Doramectin | 4% |
| Dimethyl acetamide | 15% |
| MIGLYOL 840 | 55% |
| Surfactants | 5% |
| Vaccine/adjuvant/water blend | to vol. |

In an embodiment, a neonatal vaccine component according to the instant invention comprises the ingredients as set forth in Table 9.

TABLE 9

Neonatal vaccine component

| Ingredients | Concentration (per 2 mL dose) |
|---|---|
| Bovine rotavirus, strain UK-Compton, serotype G6 P5 (inactivated) | ¼ dose of vaccine stimulates a virus neutralizing antibody titer: ≧7.7 log2/mL (guinea pigs) |
| Bovine coronavirus, strain *Medus* (inactivated) | 1/20 dose of vaccine stimulates an ELISA antibody titer: ≧3.41 log10/mL (guinea pigs) |
| *E. coli* (K99) adhesin | 1/20 dose of vaccine stimulates an ELISA antibody (OD492): >0.64 (guinea pigs) |
| Adjuvant | |
| Light Mineral Oil/Emulsifier | 1.40 mL |
| Aluminum hydroxide | 2.45-3.32 mg |
| Excipients | |
| Thiomersal | 0.051-0.069 mg |
| Other Constituents | |
| Formaldehyde | ≦0.34 mg |
| Sodium thiosulphate | Not given |
| Sodium Chloride | 0.85% w/v |
| Water for Injection | q.s |

In an embodiment, an eprinomectin solution component according to the instant invention may comprise the ingredients as set forth in Table 10 or Table 11.

TABLE 10

Eprinomectin solution component

| Ingredients | Concentration (mg/mL) | Qty. per 50 mL |
|---|---|---|
| Eprinomectin (8%) | 80 | 4.0 g |
| DMA (15%, 20% & 25%) | 150/200/250 | 7.5/10/12.5 g |
| Sorbitan Monooleate (5% & 10%) | 50/100 | 2.5/5 g |
| MIGLYOL 840 | To final volume | To final volume |

TABLE 11

Eprinomectin solution component

| Ingredients | Concentration (mg/mL) |
|---|---|
| Eprinomectin | 80 |
| DMA | 40 |
| Lecithin (6%) | 60 |
| SPAN 20 (1%) | 10 |
| MIGLYOL 840 | To final volume |

Compositions according to the instant invention may be produced by various methods using various solvent systems and surfactants. Furthermore, the identification of a suitable carrier system to produce a stable composition comprising macrocyclic lactones and other actives is challenging and unobvious. It is well known in the art that it is very difficult to formulate macrocyclic lactone active agents together with certain other actives due to different carrier requirements and the susceptibility of macrocyclic lactones to degradation in certain solvents. Avermectins and milbemycins, for instance, are poorly soluble in water and not compatible with acidic conditions, while some anthelmintic agents such as levamisole are more water soluble and require acidic pH conditions for optimum stability (see US 2006/0128641 A1). For example, U.S. Pat. No. 6,489,303 to Jancys et al. describes that mixtures of a macrocyclic lactone and an insoluble anthelmintic agent resulted in an increased rate of degradation of the macrocyclic lactone active agent, requiring the addition of excess antioxidant to stabilize the mixture. Therefore, the combination of a complex, multi-component neonatal vaccine and a macrocyclic lactone, in a single liquid composition that is both stable and efficacious against a broad spectrum of endoparasites, and at the same time elicits pathogen-specific immune responses, represents a significant achievement in the field of veterinary medicine that is neither predictable nor obvious.

Of particular experimental challenge was establishing a solvent system that could adequately dissolve the relatively high concentrations of eprinomectin that are required for the compositions to deliver an effective dose to the animals. In fact, only through the inventive methods disclosed herein could the high concentration of the eprinomectin be blended with immunogenic components, such as the neonatal vaccine components discussed above. Rigorous experimentation established that eprinomectin could not be added to the immunogenic components unless the eprinomectin was first dissolved into the solvent component and then combined with the immunogenic components resulting in emulsions according to the instant invention.

In an embodiment, combination compositions according to the instant invention may be manufactured by combining equal volumes of eprinomectin solution components with immunogenic or neonatal vaccine components. In an embodiment, about 2 mL of neonatal vaccine component is combined with about 2 mL of eprinomectin solution to produce about 4 mL of a combination composition, which will also be referred to herein as a "final product".

In another embodiment, a water phase for an immunogenic or neonatal vaccine component of the instant invention may be prepared according to the steps comprising: (a) adding injectable water; (b) adding THIOMERSAL; (c) mixing until clear; (d) adding sodium thiosulphate; (e) mixing until clear; (f) adding sodium chloride; (g) mixing until clear; (h) adding formaldehyde; (i) mixing until clear; (j) adding antigen concentrates, which may be derived from rotavirus and coronavirus; (k) bringing to volume with injectable water to form the water phase. In another embodiment, the water phase is combined with an oily phase, forming an emulsion, which is the immunogenic or neonatal vaccine component of the instant invention. The emulsion may be prepared using light mineral oil or other suitable emulsifier and may be have an off-white appearance.

In an embodiment, compositions according the instant invention may be smooth white or off-white liquid emulsions with acceptable syringeability. Any separation may be easily resuspended with gentle shaking, even when compositions are at about 2-8° C.

In an embodiment, the vaccine component may be prepared from virus and/or bacteria originally obtained in the field, and more specifically, may be prepared from various combinations of bovine coronavirus, bovine rotavirus and *E. coli* originally obtained in the field. One skilled in the art can readily obtain other appropriate strains from suitable depositories, academic or commercial sources.

In another embodiment, viral fractions of the invention, the viruses were cultivated in cell culture from about 35° C. to about 39° C., or about 37° C. The virus was then harvested and inactivated with an inactivating agent which does not destroy the virus particles or antigenicity according to standard methods known to the art.

The production of the bacterial fractions similarly involved a process of growing the bacterial organism in a growth medium to produce large amounts of toxins. These are then harvested and inactivated with an inactivating agent. When injected into the animal these "toxoids" become antigens which the immune system recognizes as foreign, thereby triggering antibody production.

Compositions in forms for various administration routes are envisioned by the invention. And again, the effective dosage and route of administration are determined by known factors, such as age, sex, weight, and other screening procedures which are known and do not require undue experimentation. Dosages of each active agent can be as in herein cited documents (or documents referenced or cited in herein cited documents).

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

The invention will now be further described by way of the following non-limiting examples.

EXAMPLES

Without further elaboration, it is believed that one skilled in the art can, using the preceding descriptions, practice the present invention to its fullest extent. The following detailed examples are to be construed as merely illustrative, and not limitations of the preceding disclosure in any way whatsoever. Those skilled in the art will promptly recognize appropriate variations from the procedures both as to reactants and as to reaction conditions and techniques.

Example 1

Production and Quality of Various Combination Vaccine/Macrocyclic Lactone Compositions Various combinations of macrocyclic lactone solvent components and surfactants were tested to identify ingredients and methods which could give rise to stable combination compositions according to the instant invention. For the initial development phase, commercially prepared vaccine (ROTAVEC Corona, Intervet) was used as the neonatal vaccine component for the finished formulation/combination composition. The eprinomectin solution component was prepared according to the following steps:

(a) added DMA and MIGLYOL; (b) added eprinomectin; (c) mixed until the solution was clear; (d) added lecithin; (e) mixed until the solution was clear; (f) added SPAN; (g) mixed until the solution was clear; (h) added MIGLYOL to bring solution to between 85% and 95% final solution volume; (i) warmed the DMA/MIGLYOL/Eprinomectin/Lecithin/SPAN solution to between 50° C. and 60° C.; (j) cooled the solution to below 30° C. and then mixing until the solution is clear; (k) adjusted the volume to the final solution volume by adding MIGLYOL; and (l) aseptically filtered through a 0.22 μm filter.

The development of the eprinomectin solution component posed significant experimental challenges due to the need to incorporate a relatively high loading of the active. A variety of excipients were tested to arrive at the preferred formulation. Tables 12-15 summarize the components and results (e.g. visual inspection of the emulsion compositions) for lab batch formula series A and B.

TABLE 12

Batch A series eprinomectin solution component

|  | Concentration (mg/mL) | Qty. per 50 mL |
|---|---|---|
| Eprinomectin (8%) | 80 | 4.0 g |
| DMA (15%, 20% & 25%) | 150/200/250 | 7.5/10/12.5 g |
| Sorbitan Monooleate (5% & 10%) | 50/100 | 2.5/5 g |
| MIGLYOL 840 | Q.s | Q.s |

TABLE 13

Batch A series composition and visual appearance

| | Constituents of Eprinomectin Concentrate Component | | | | Observation |
|---|---|---|---|---|---|
| Batch | Eprinomectin (% w/v) | DMA (% w/v) | Sorbitan Monooleate (% w/v) | MIGLYOL 840 (% w/v) | (2 days after mixing with neonatal vaccine component) |
| 01 | 8 | 15 | 10 | Q.s to 100 | Separation of DMA layer & antigen solidify |
| 02 | 8 | 20 | 10 | Q.s to 100 | Separation of DMA layer & antigen solidify |
| 03 | 8 | 25 | 10 | Q.s to 100 | Separation of DMA layer & antigen solidify |
| 04 | 8 | 15 | 5 | Q.s to 100 | Separation of DMA layer & antigen solidify |
| 05 | 8 | 20 | 5 | Q.s to 100 | Separation of DMA layer & antigen solidify |
| 06 | 8 | 25 | 5 | Q.s to 100 | Separation of DMA layer & antigen solidify |
| 07 | 8 | 10 | 5 | Q.s to 100 | Separation of DMA layer & antigen solidify |
| 08 | 8 | 10 | 10 | Q.s to 100 | Separation of DMA layer & antigen solidify |
| 16 | 8 | 10 | 5% SMO + 5% TWEEN | Q.s to 100 | Separation of DMA layer & antigen solidify |
| 18 | 8 | 10 | 10% SPAN 20 | Q.s to 100 | Separation of DMA layer & antigen solidify |

TABLE 14

Batch B series eprinomectin solution component

|  | Concentration (mg/mL) | Qty. per 50 mL |
|---|---|---|
| Eprinomectin | 80 | 4.0 g |
| DMA (15%, 10% & 8%) | 150/100/80 | 7.5/5/4 g |
| Lecithin (6%) | 60 | 3.0 g |
| SPAN 20 (1%) | 10 | 0.5 g |
| TWEEN 80 (2%) | 20 | 1.0 g |
| MIGLYOL 840 | Q.s | Q.s |

TABLE 15

Batch B series composition and visual appearance

| Batch | Eprinomectin (% w/v) | DMA (% w/v) | Lecithin (% w/v) | MIGLYOL 840 (% w/v) | Observation (2 days after mixing with neonatal vaccine component) |
|---|---|---|---|---|---|
| 09 | 8 | 15 | 5 | Q.s to 100 | Separation of DMA layer & antigen solidify |
| 10 | 8 | 10 | 3 | Q.s to 100 | Physical appearance is not elegant |
| 11 | 8 | 10 | 2 | Q.s to 100 | Physical appearance is not elegant |
| 12 | 8 | 8 | 2 | Q.s to 100 | Physical appearance is not elegant |
| 13 | 8 | 8 | 3 | Q.s to 100 | Physical appearance is not elegant |
| 14 | 8 | 8 | 5 | Q.s to 100 | Physical appearance is not elegant |
| 15 | 8 | 8 | 10 | Q.s to 100 | Physical appearance is not elegant |
| 17 | 8 | 8 | 8 | Q.s to 100 | Physical appearance is not elegant |
| 19 | 8 | 6 | 5 | Q.s to 100 | Physical appearance is not elegant |
| 20 | 8 | 8 | 6% Leci + 2% TWEEN 80 | Q.s to 100 | Separation of DMA layer & antigen solidify |
| 21 | 8 | 8 | 6% Leci + 2% SPAN 20 | Q.s to 100 | Good |
| 22 | 8 | — | — | Q.s 100 (PGMC) | Eprinomectin precipitate |
| 23 | 8 | 8 | 6% Leci + 1% SPAN 20 | Q.s to 100 | Good |
| 24 | 8 | 8 | 5% Leci + 2% SPAN 20 | Q.s to 100 | Good |
| 25 | 8 | — | — | Q.s to 100 | Eprinomectin precipitate & solidify |
| 26 | 8 | — | — | Q.s 100 (Mig 810) | Eprinomectin precipitate |
| 27 | 8 | — | 6% Leci + 1% SPAN 20 | Q.s to 100 | Good |
| 28 | 8 | — | 5% Leci + 2% SPAN 20 | Q.s to 100 | Good |
| 29 | 8 | 8 | 6% Leci + 1% SPAN 20 | Q.s to 100 | Good |
| 30 | 8 | 8 | 5.5% Leci + 1.5% SPAN | Q.s to 100 | Good |
| 31 | 8 | 8 | 5% Leci + 2% SPAN 20 | Q.s to 100 | Good |
| 32 | 8 | 4 | 6% Leci + 1% SPAN 20 | Q.s to 100 | Best formulation based on physical observation |
| 33 | 8 | 4 | 5.5% Leci + 1.5% SPAN | Q.s to 100 | Good |
| 34 | 8 | 4 | 5% Leci + 2% SPAN 20 | Q.s to 100 | Good |

Further, DMA is present in most of the formulations which had at least an appearance of "good" after 2 days, but several "good" formulations did not possess DMA (see for example Batch B numbers 27 and 28). Lecithin by itself did not appear sufficient to produce "good" formulations (see for example Batch B numbers 9-19, and addition of TWEEN to the Lecithin containing composition did not appear to alleviate the problem (see Batch B number 20). Lecithin and SPAN were present in all formulations which were evaluated to be at least "good" after 2 days. Of the tested combinations of ingredients tested, Batch B number 32 was the best formulation based on physical observation.

Example 2

ML Residues in Milk and Tissue of Lactating Dairy Cows after Single Dose Administration of Levamisole/Eprinomectin Formulations Study Objectives: 1) To measure ML residues in milk and tissues of lactating dairy cows after a single dose of an experimental formulation of eprinomectin, ivermectin, moxidectin or doramectin combined with an inactivated rotavirus, coronavirus and *Escherichia coli* vaccine was administered by intramuscular injection at 0.3 and 0.4 mg macrocyclic lactone/kg bodyweight. 2) To evaluate local tissue irritancy of the experimental formulations when administered to cattle by intramuscular injection.

Background: Formulations according to the instant description are intended to be administered to cows via intramuscular injection up to 3 weeks prior to calving. It was therefore necessary to determine whether treatment with such a product under the proposed regime would result in ML residues in milk after calving.

Experimental Design: Dairy cows were selected according to summary information provided in Table 16. Experimental formulations of each of four macrocyclic lactones were separately combined with equal parts of a registered vaccine, Rotavec® Corona (Schering-Plough). The recommended dose of Rotavec® Corona is 2 mL per animal, which was diluted to produce 4 mL of ML/vaccine combination. Each ML/vaccine combination contained 40 mg/mL macrocyclic lactone. The amount of ML in the formulations is summarized in Table 17.

TABLE 16

Experimental dairy cow summary information

| Species: | Dairy cows |
|---|---|
| Breed | Friesian and Friesian cross |
| Number: | 33 |
| Age: | Open |
| Weight: | 415-576 kg |
| Milk yield: | Delivering ≧ 16.1 liters per day (7-day average) |
| Other: | Healthy; no evidence of mastitis (RMT and palpation Day −5) |

TABLE 17

Experimental dairy cow summary information

| Name | Active ingredient/s and concentration | CAS | Route | Withholding period |
|---|---|---|---|---|
| Eprinomectin injection | Eprinomectin 40.17 mg/mL | Eprinomectin 123997-26-2 | IM injection | Meat 91 days Milk 35 days |
| Ivermectin injection | Ivermectin 44.04 mg/mL | Ivermectin 70288-86-7 | | |
| Moxidectin injection | Moxidectin 40.73 mg/mL | Moxidectin 113507-06-5 | | |
| Doramectin injection | Doramectin 38.86 mg/mL | Doramectin 117704-25-3 | | |

*Rotavec ® Corona is a registered inactivated vaccine (Schering-Plough, A8132) containing the following antigens:
Bovine coronavirus (inactive);
Bovine rotavirus (inactive);
*Escherichia coli* K99 (pili)

Methods: On day −5, fifty-four animals were identified for screening and were checked for mastitis by palpation of the mammary gland, visualization of the mammary secretions and Rapid Mastitis Test (RMT, Immucell, Portland, Me.). Individual milk samples were collected for somatic cell count (SCC) and thirty-three animals that met the inclusion criteria were selected for the study. Of the thirty-three animals, the cow with the highest average daily milk yield, as assessed over a seven-day period, was allocated as the control. The remaining thirty-two animals were ranked from highest to lowest on average daily milk yield, over the same time period, and divided into four blocks of eight animals each. A random number was generated for each animal using the Microsoft Excel random number generator function. Within each block, the lowest random number was allocated to Group 1, the second lowest to Group 2 and sequentially through to Group 8, creating eight groups of four animals each (Table 18).

On Day 0, the cows were weighed and blood samples were collected from all animals in Groups 1 and 2 for use in a subsequent plasma eprinomectin assay. The blood samples were stored frozen at or colder than −18° C. pending laboratory analysis. Each animal was treated with the indicated formulation at the appropriate dose rate. Doses were calculated based upon the animal's Day 0 bodyweight to provide approximately 40 mg ML/mL. Calculated doses were rounded up to the nearest 0.2 mL.

The formulations were administered by deep intramuscular injection in the anterior neck region. Injection sites were clean and dry and inspected for lesions prior to injection. Injections were administered with a different 10 mL syringe for each product. A sterile 18 gauge 1½ inch needle was used for each injection. The time of treatment was recorded. Evidence of pain on injection was assessed. Cows were observed for adverse reactions to the formulations at approximately 30 minutes, 2 and 4 hours after treatment.

TABLE 18

Treatment groups

| Group | n | ML | Nominal dose rate | Route |
|---|---|---|---|---|
| 1 | 4 | Eprinomectin | 0.3 mg/kg | IM |
| 2 | 4 | Eprinomectin | 0.4 mg/kg | IM |
| 3 | 4 | Ivermectin | 0.3 mg/kg | IM |
| 4 | 4 | Ivermectin | 0.4 mg/kg | IM |
| 5 | 4 | Moxidectin | 0.3 mg/kg | IM |
| 6 | 4 | Moxidectin | 0.4 mg/kg | IM |
| 7 | 4 | Doramectin | 0.3 mg/kg | IM |
| 8 | 4 | Doramectin | 0.4 mg/kg | IM |
| 9 | 1 | Negative Control | NA | NA |

Blood samples were collected from all animals in Groups 1 and 2 for plasma eprinomectin assay on Days 1, 3 and 7 and stored frozen as described. The time of blood collection was recorded. Herd test equipment (De Laval) was used to collect an approximately 2% sample representative of the entire milking for each individual cow at the morning milking on each of Days 1-10 following treatment, and at the morning milking on Days 14, 21 and 35. Duplicate subsamples were decanted for each cow in Groups 1-4 and 7-9 and triplicate subsamples were decanted for each cow in Groups 5-6. Each sample from treated animals measured approximately 30 mL. The start and finish times for each milking of the 33 study animals were recorded to give an estimate of the actual time of milk sample collection.

The study animals were milked after the main herd. The milk line was thoroughly flushed with cold water prior to milking the study animals. The herd test equipment was cleaned between samplings. It was washed "in-line" with the milking plant wash. Sample vessels were then further cleaned through a dishwasher. The sampler connections were further cleaned by soaking in hot acid, then rinsed. Milk yields at each milking at which samples were collected were measured and recorded.

Observations: Animals were observed for general behavior and demeanor on Days 1-10. Injection sites were examined by inspection and palpation at the morning milking on Days 1, 3, 7 and 14. Any visible or palpable reactions were described and measured (width, length and depth). Reactions that persisted after day 14 were re-evaluated on Day 21.

Milk was withheld from the vat until Day 35.

Figure 2:
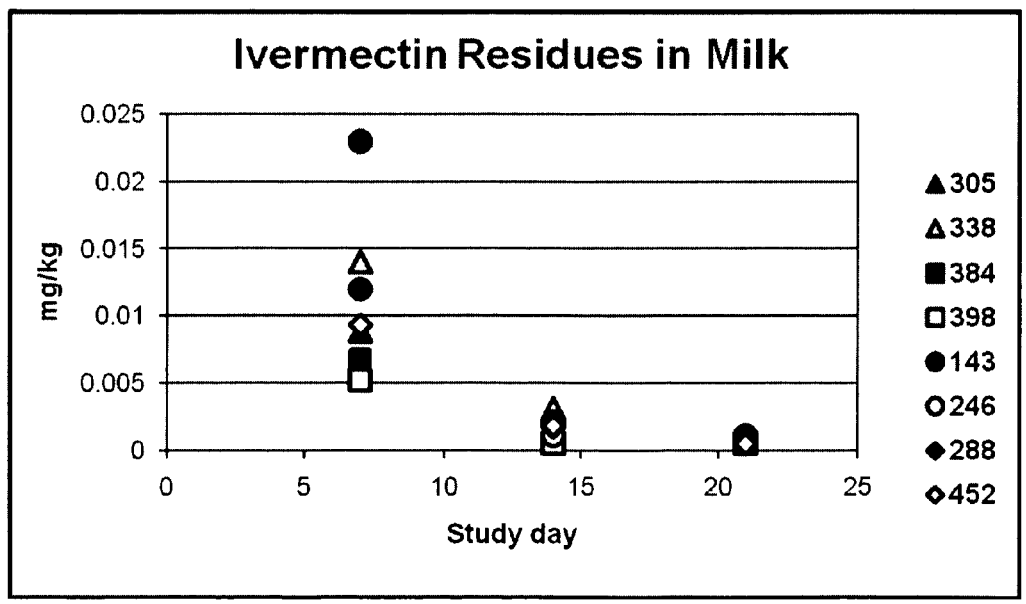
FIG. 2 is a graph of ivermectin residues in milk
Figure 3:
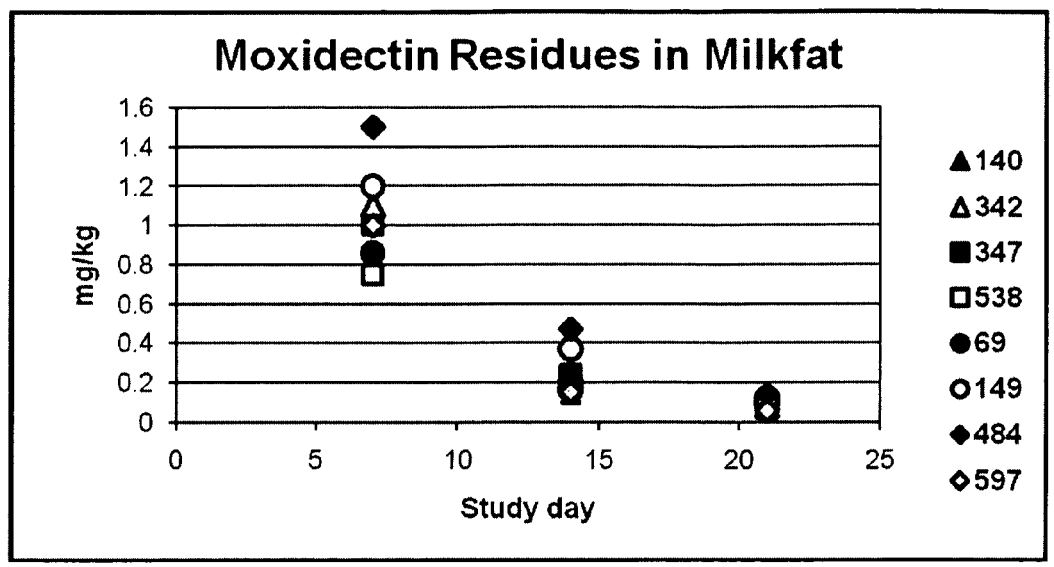
FIG. 3 is a graph of moxidectin residues in milkfat
Figure 4:
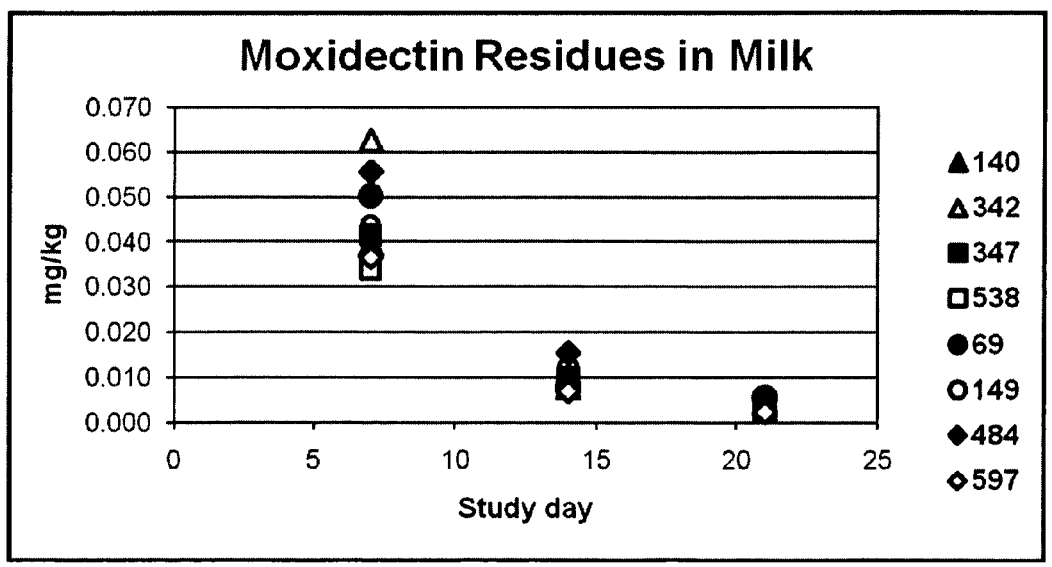
FIG. 4 is a graph of moxidectin residues in whole milk
Figure 5:
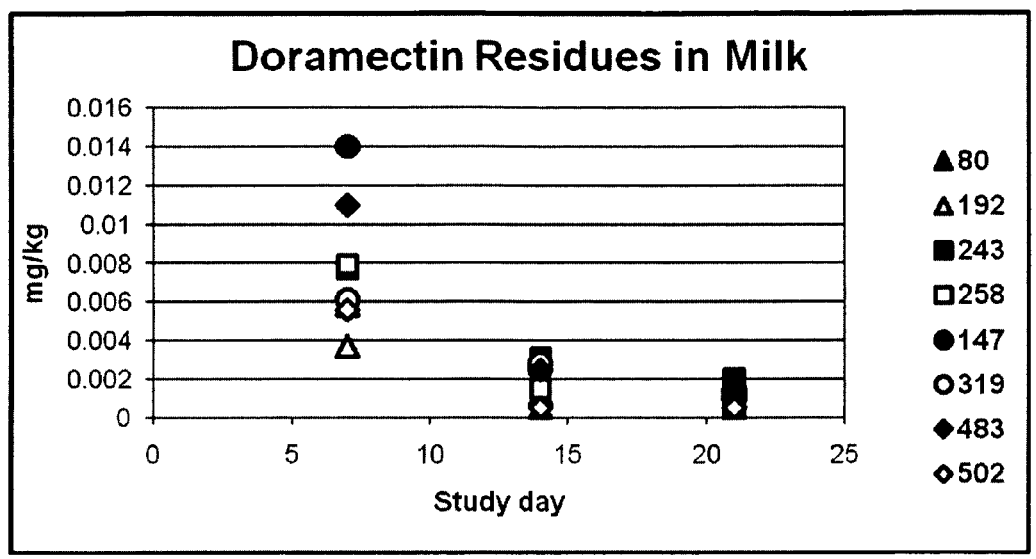
FIG. 5 is a graph of doramectin residues in milk
Figure 6:
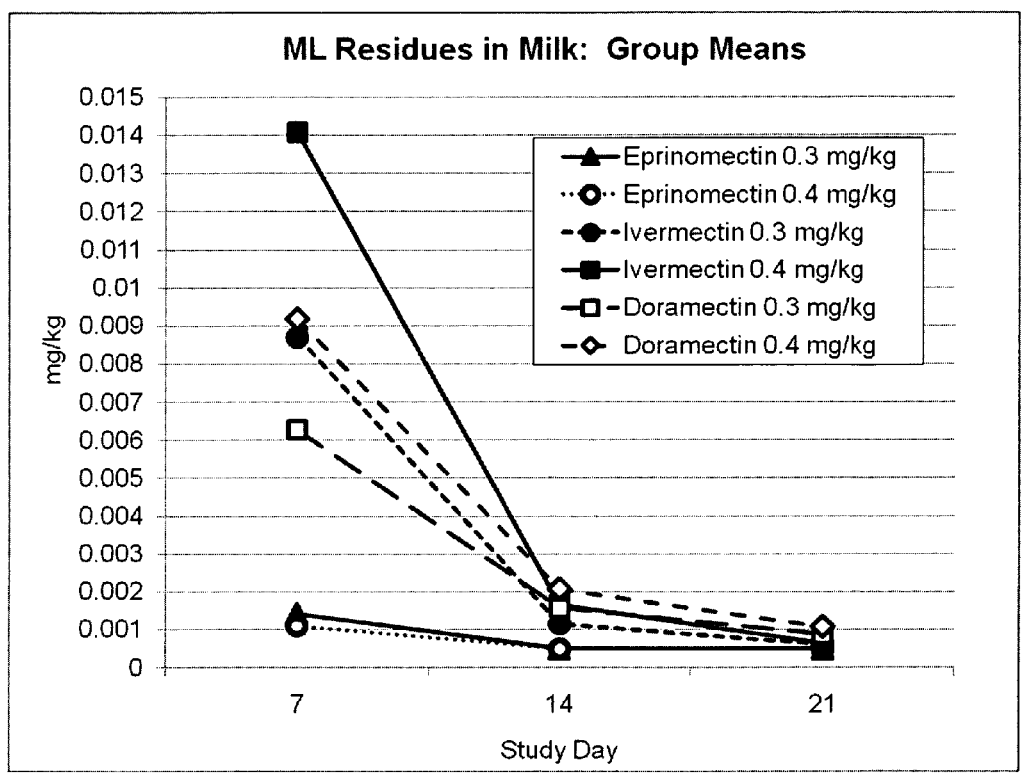
FIG. 6 is a graph of group mean residues in milk (eprinomectin, ivermectin, doramectin)
Figure 7:
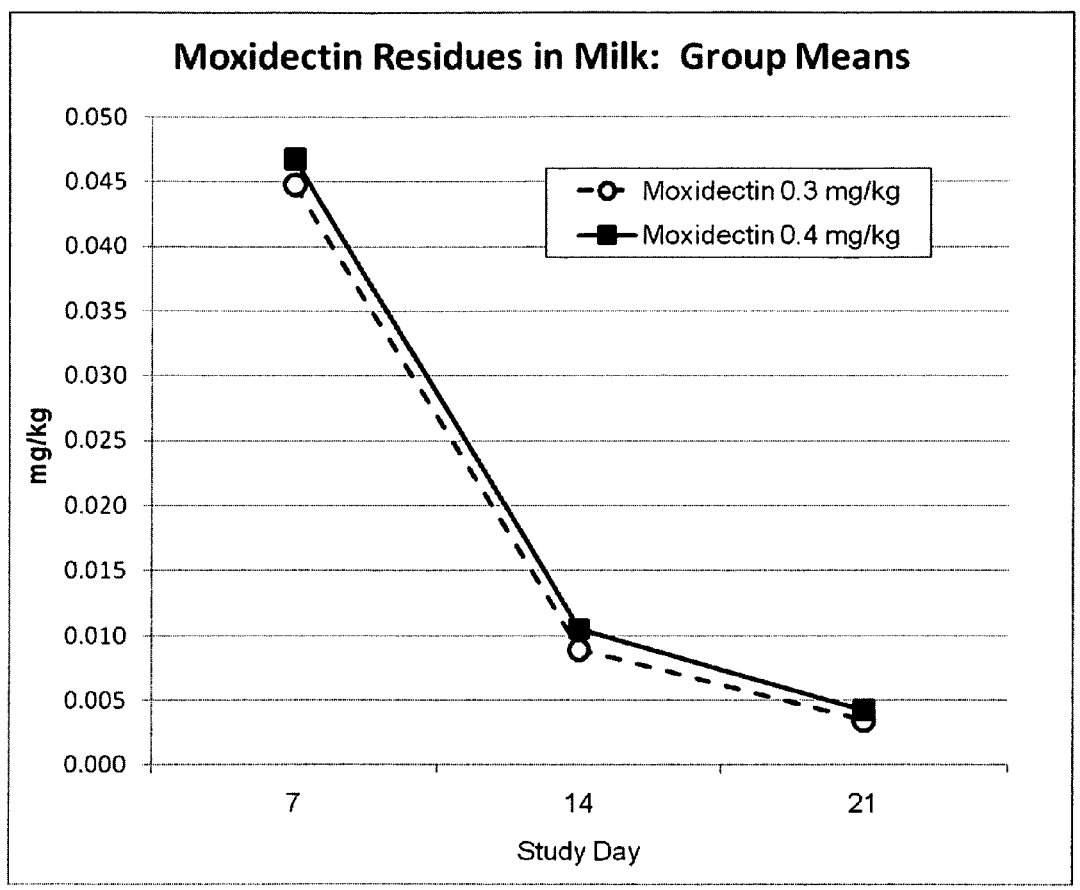
FIG. 7 is a graph of group mean moxidectin residues in whole milk

Analysis: One milk sample from each cow in Groups 5 and 6 at each timepoint was refrigerated at 2-8° C. and couriered (fresh, chilled) to the Livestock Improvement Corporation Testlink laboratory, Hamilton, New Zealand, for milkfat quantification using a fluorometric method (Fossomatic). Two samples from each cow at each timepoint were frozen at or colder than −18° C. Primary samples were couriered to Hill Laboratory, Ruakura New Zealand in frozen state and assayed for the relevant ML residues using a validated method (acetonitrile extraction, SPE cleanup and analysis by LC-MS/MS). Samples from the Day 7, 14 and 21 milkings were assayed first. The results are presented in Table 21 and in FIGS. 1-7. Reserve milk samples were retained until the assays were completed. The blood samples were centrifuged and the plasma decanted and stored frozen at or colder than −18° C. Samples from the control animal measured approximately 90 mL. Control samples were analyzed for ML residues to provide a baseline comparison to the treated groups. The surplus milk from the control animal was used by the laboratory to create spiked QC samples.

Results: Somatic cell counts performed on samples collected on Day −5 averaged 76,500 cells/mL across all study animals and ranged from 18,000 to 144,000 cells/mL. The individual cow average daily milk yield over the seven-day pre-study period averaged 17.6 L/day across all study animals and ranged from 16.1 to 19.7 L/cow/day. Bodyweights measured on Day 0 averaged 482.1 kg across all study animals and ranged from 415 to 576 kg. Dose rates were calculated at 0.3 mg/kg or 0.4 mg/kg based on an ML concentration of 40 mg/mL. The actual dose rates (adjusted for actual ML concentration as determined by the Certificate of Analyses) are as shown in Table 19.

TABLE 19

Actual dose rates (mg/kg)

| | Eprinomectin | Ivermectin | Moxidectin | Doramectin |
|---|---|---|---|---|
| Concentration (mg/mL) | 40.17 | 44.039 | 40.73 | 38.86 |
| Intended dose (mg/kg) | 0.3 | 0.3 | 0.3 | 0.3 |
| Actual dose (mg/kg) | 0.30 | 0.33 | 0.31 | 0.29 |
| Intended dose (mg/kg) | 0.4 | 0.4 | 0.4 | 0.4 |
| Actual dose (mg/kg) | 0.40 | 0.44 | 0.41 | 0.39 |

Animals were treated between 08:55 and 10:03 on the morning of Day 0. Morning milking commenced at or after 07:30 and concluded at or before 08:09 on each day that samples were collected during the period up to Day 21. No animals showed signs of pain on injection with any of the formulations. No adverse events were observed after treatment. Injection site reaction measurements on Days 1, 3, 7, 14 and 21 are shown in Table 22. Reactions were firm, discrete swellings of the muscular tissue that did not appear to be painful with light palpation. One animal in each of Group 1 (eprinomectin 0.3 mg/kg), Group 2 (eprinomectin 0.4 mg./kg) and Group 6 (moxidectin 0.3 mg/kg) had injection site reactions that persisted at least until 21 days after treatment.

Discussion: Intramuscular injection with Rotavec® Corona caused injection site reactions in several animals. Injection site reaction of this nature is recognized on the label and package inserts for Rotavec® Corona, and is suggested to be due to the oil in the vaccine. Thus, the Rotavec® Corona component of the inventive formulation likely contributed to the reactions observed in the study.

The Maximum Residue Limits (MRL) for MLs in bovine milk are presented in Table 20. The European Medicines Agency (EMEA) currently prohibits the use of doramectin and ivermectin in bovines producing milk for human consumption—no residues of these actives are permitted. Codex Alimentarius sets a MRL for eprinomectin, doramectin and ivermectin in bovine milk but does not set a MRL for moxidectin in bovine milk. New Zealand's ACVM has set MRLs for all four actives in bovine milk, which reflect the international MRLs where available. The ACVM MRL for moxidectin defines the residue as moxidectin in milk fat whereas the EMEA MRL for moxidectin defines the residue as moxidectin in whole milk.

TABLE 20

Bovine milk MRLs (mg/kg)

| ML | Definition LOQ | ACVM MRL | Codex MRL | EMEA |
|---|---|---|---|---|
| Eprinomectin | Eprinomectin B1a | 0.02 | 0.02 | 0.02 |
| Ivermectin | Ivermectin B1a | 0.01 | 0.01 | * |
| Moxidectin | Moxidectin | 1.0 (in milk fats) | No MRL set | 0.04 (in milk) |
| Doramectin | Doramectin | 0.015 | 0.015 | * |

* Not for use in bovines producing milk for human consumption (i.e. < LOQ)

Conclusion: Eprinomectin residues for all study animals were below the MRL of 0.02 mg/kg (by a factor of ten) at 7 days after treatment and below the limit of quantitation (LOQ) at 14 days after treatment. Residues measuring near or above the ACVM MRLs were detected at 7 days after treatment with doramectin, moxidectin and ivermectin. Residues measuring above the LOQ (and therefore above the EMEA tolerance for doramectin and ivermectin) were detected at 21 days after treatment with doramectin, moxidectin and ivermectin. Based on these data, and relative to the MRLs that apply in Europe, the withholding period for the eprinomectin formulation is estimated at 7 days. The withholding period for the variants containing moxidectin, ivermectin and doramectin are expected to be more than 21 days and possibly up to 28 days for moxidectin.

TABLE 21

ML residue by cow for days 7, 14, and 21 (in mg/kg)

| Group | Residues assayed | Cow | Day 7 | Day 14 | Day 21 |
|---|---|---|---|---|---|
| 1 | Eprinomectin B1a | 379 | 0.0012 | <0.0010 | <0.0010 |
|   |   | 421 | 0.0017 | <0.0010 | <0.0010 |
|   |   | 432 | <0.0010 | <0.0010 | <0.0010 |
|   |   | 563 | 0.0023 | <0.0010 | <0.0010 |
| 2 | Eprinomectin B1a | 67 | 0.0013 | <0.0010 | <0.0010 |
|   |   | 75 | <0.0010 | <0.0010 | <0.0010 |
|   |   | 336 | 0.0021 | <0.0010 | <0.0010 |
|   |   | 463 | <0.0010 | <0.0010 | <0.0010 |
| 3 | Ivermectin B1a | 305 | 0.0088 | <0.0010 | <0.0010 |
|   |   | 338 | 0.014 | 0.0031 | 0.0010 |
|   |   | 384 | 0.0068 | <0.0010 | <0.0010 |
|   |   | 398 | 0.0052 | <0.0010 | <0.0010 |
| 4 | Ivermectin B1a | 143 | 0.023 | 0.0021 | 0.0011 |
|   |   | 246 | 0.012 | 0.0011 | <0.0010 |
|   |   | 288 | 0.012 | 0.0017 | <0.0010 |
|   |   | 452 | 0.0093 | 0.0018 | <0.0010 |
| 5 | Moxidectin In milk fat | 140 | 0.80 | 0.14 | 0.059 |
|   |   | 342 | 1.1 | 0.26 | 0.080 |
|   |   | 347 | 1.0 | 0.24 | 0.068 |
|   |   | 538 | 0.75 | 0.18 | 0.075 |
|   | Moxidectin In whole milk | 140 | 0.040 | 0.0078 | 0.0026 |
|   |   | 342 | 0.063 | 0.010 | 0.0040 |
|   |   | 347 | 0.042 | 0.0099 | 0.0031 |
|   |   | 538 | 0.034 | 0.0079 | 0.0041 |
| 6 | Moxidectin In milk fat | 69 | 0.86 | 0.17 | 0.091 |
|   |   | 149 | 1.2 | 0.37 | 0.12 |
|   |   | 484 | 1.5 | 0.47 | 0.14 |
|   |   | 597 | 1.0 | 0.15 | 0.057 |
|   | Moxidectin In whole milk | 69 | 0.050 | 0.0081 | 0.0055 |
|   |   | 149 | 0.044 | 0.012 | 0.0037 |
|   |   | 484 | 0.056 | 0.015 | 0.0055 |
|   |   | 597 | 0.037 | 0.0069 | 0.0023 |
| 7 | Doramectin | 80 | 0.0058 | <0.0010 | <0.0010 |
|   |   | 192 | 0.0037 | 0.0012 | <0.0010 |
|   |   | 243 | 0.0077 | 0.0031 | 0.0020 |
|   |   | 258 | 0.0079 | 0.0015 | <0.0010 |
| 8 | Doramectin | 147 | 0.014 | 0.0025 | 0.0010 |
|   |   | 319 | 0.0061 | 0.0028 | 0.0014 |
|   |   | 483 | 0.011 | 0.0025 | 0.0014 |
|   |   | 502 | 0.0056 | <0.0010 | <0.0010 |
| 9 | Eprinomectin B1a | 381 | <0.0010 | <0.0010 | <0.0010 |
|   | Ivermectin B1a | 381 | <0.0010 | <0.0010 | <0.0010 |
|   | Moxidectin in milk fat | 381 | <0.0200 | <0.0200 | <0.0200 |
|   | Moxidectin in whole milk | 381 | <0.0010 | <0.0010 | <0.0010 |
|   | Doramectin | 381 | <0.0010 | <0.0010 | <0.0010 |

TABLE 22

Injection site reaction measurements

| Group | Treatment | Cow | Day 1 | Day 3 | Day 7 | Day 14 | Day 21 |
|---|---|---|---|---|---|---|---|
| 1 | EPN 0.3 mg/kg | 379 | 40 × 50 × 5 | 70 × 110 × 10 | 50 × 50 × 15 | 30 × 30 × 10 | 20 × 20 × 10 |
|   |   | 421 | 60 × 40 × 5 | — | — | — | — |
|   |   | 432 | — | | | | |
|   |   | 563 | — | | | | |
|   |   | Count | 0 | 1 | 1 | 1 | 1 |
| 2 | EPN 0.4 mg/kg | 67 | 80 × 110 × 10 | 80 × 110 × 10 | 90 × 110 × 15 | 70 × 90 × 15 | 70 × 70 × 10 |
|   |   | 75 | 70 × 110 × 10 | 40 × 50 × 5 | — | — | — |
|   |   | 336 | — | | | | |
|   |   | 463 | — | | | | |
|   |   | Count | 2 | 2 | 1 | 1 | 1 |
| 3 | INV 0.3 mg/kg | 305 | — | | | | |
|   |   | 338 | — | | | | |
|   |   | 384 | 40 × 50 × 5 | — | — | — | — |
|   |   | 398 | — | | | | |
|   |   | Count | 1 | 0 | 0 | 0 | 0 |
| 4 | IVN 0.4 mg/kg | 143 | — | | | | |
|   |   | 246 | — | | | | |
|   |   | 288 | — | | | | |
|   |   | 452 | — | | | | |
|   |   | Count | 0 | 0 | 0 | 0 | 0 |

TABLE 22-continued

Injection site reaction measurements

| Group | Treatment | Cow | Day 1 | Day 3 | Day 7 | Day 14 | Day 21 |
|---|---|---|---|---|---|---|---|
| 5 | Moxidectin 0.3 mg/kg | 140 | — | — | — | — | — |
| | | 342 | — | — | — | — | — |
| | | 347 | — | — | — | — | — |
| | | 538 | — | — | — | — | — |
| | | Count | 0 | 0 | 0 | 0 | 0 |
| 6 | Moxidectin 0.4 mg/kg | 69 | 120 × 130 × 1 | 90 × 90 × 10 | 80 × 80 × 10 | 60 × 60 × 10 | 80 × 60 × 15 |
| | | 149 | — | — | — | — | — |
| | | 484 | — | — | — | — | — |
| | | 597 | — | — | — | — | — |
| | | Count | 1 | 1 | 1 | 1 | 0 |
| 7 | Doramectin 0.3 mg/kg | 80 | 40 × 50 × 5 | — | 40 × 40 × 5 | — | — |
| | | 192 | 40 × 50 × 10 | 20 × 20 × 5 | 10 × 10 × 5 | — | — |
| | | 243 | — | — | — | — | — |
| | | 258 | — | — | — | — | — |
| | | Count | 2 | 1 | 2 | 0 | 0 |
| 8 | Doramectin 0.4 mg/kg | 147 | — | 10 × 10 × 5 | — | — | — |
| | | 319 | — | — | — | — | — |
| | | 483 | — | — | — | — | — |
| | | 502 | — | — | — | — | — |
| | | Count | — | — | — | — | — |
| 9 | No Injection | 381 | — | — | — | — | — |
| | | Count | 0 | 0 | 0 | 0 | 0 |

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

As the non-limiting examples above demonstrate, the compositions of the invention comprising at least one macrocyclic lactone active agent and at least one neonatal vaccine component show superior stability. The invention is further described by the following claims.

What is claimed is:

1. An injectable composition for preventing or controlling parasitic, bacterial, or viral infections or diseases in cattle, the composition comprising:
    (a) an effective amount of at least one inactivated rotavirus or coronavirus viral component,
    (b) an effective amount of at least one macrocyclic lactone active compound,
    (c) a suitable carrier, wherein the carrier comprises a pharmaceutically acceptable solvent system for the macrocyclic lactone, and which system comprises dimethylacetamide and a propylene glycol diester of caprylic and capric acids ("the solvents"); and a sorbitan monolaurate, a lecithin, or both ("the surfactant(s)"), and
    (d) a preservative.

2. The composition of claim 1 wherein the macrocyclic lactone active is abamectin, doramectin, eprinomectin, ivermectin, or moxidectin.

3. The composition of claim 1 wherein the macrocyclic lactone is eprinomectin.

4. The composition of claim 1 which further comprises an E. coli bacterin-toxoid.

5. The composition of claim 1, wherein the composition is in the form of a dosage form.

6. The composition of claim 5 wherein a single dose volume is effective for the treatment of cows weighing from about 400 kg to about 800 kg.

7. The composition of claim 5 wherein a dose volume is capable of delivering at least about 200 μg/kg of macrocyclic lactone to cows weighing from about 400 kg to about 800 kg and wherein the composition comprises eprinomectin or ivermectin.

8. The composition of claim 1 wherein the composition comprises abamectin, doramectin, eprinomectin, ivermectin or moxidectin at a concentration of between about 2% to about 6% w/v of the composition.

9. The composition of claim 8 wherein the concentration is about 3% to about 5%.

10. The composition of claim 8 wherein the concentration is about 3.5% to about 4.5% or about 3.5% to about 4%.

11. The composition of claim 7 wherein the dose volume prevents the macrocyclic lactone active compound dose exceeding a dose of 400 μg/kg.

12. The composition of any one of claims 1-3 wherein the surfactant(s) comprise both the sorbitan monolaurate and the lecithin.

13. The composition of claim 12, wherein the sorbitan monolaurate is present in an amount of about 1% to about 2% (w/v) and the lecithin is present in an amount of about 5% to about 6% (w/v).

14. The composition of claim 13, wherein the sorbitan monolaurate is present in an amount of about 1% (w/v) and the lecithin is present in an amount of about 6% (w/v).

15. The composition of claim 12, wherein the dimethylacetamide is present in an amount of about 4% to about 8%.

16. A method of preparing the composition of claim 1 comprising the steps of:
    a. preparing a macrocyclic lactone solution component by completely dissolving the macrocyclic lactone in the pharmaceutically acceptable solvent system;
    b. preparing a neonatal vaccine component comprising at least one inactivated rotavirus or coronavirus component; and
    c. blending the components of (a) and (b) together to produce the composition of claim 1.

17. The method of claim 16 wherein the preparing a macrocyclic lactone solution component step comprises the steps of:
    a. adding dimethylacetamide and a propylene glycol diester of caprylic and capric acids;
    b. adding eprinomectin;

c. mixing until the solution is clear;
d. adding lecithin;
e. mixing until the solution is clear;
f. adding a sorbitan monolaurate;
g. mixing until the solution is clear;
h. adding the propylene glycol diester of caprylic and capric acids to bring solution to between about 85% and about 95% of the final solution volume;
i. warming the dimethylacetamide/propylene glycol diester of caprylic and capric acids/Eprinomectin/Lecithin/sorbitan monolaurate solution to between about 45° C. and about 65° C.;
j. cooling the solution to below about 35° C. or to below about 0° C. and then mixing until the solution is clear;
k. adjusting volume to the final solution volume by adding the propylene glycol diester of caprylic and capric acids; and
l. aseptically filtering through a 0.22 μm filter to prepare the eprinomectin solution component.

18. A method of preventing or controlling parasitic diseases in pregnant cows and viral diseases in neonatal calves by parenterally administering to the pregnant cow an effective amount of the composition of claim 1.

* * * * *